(12) United States Patent
Pachl et al.

(10) Patent No.: US 8,163,560 B2
(45) Date of Patent: Apr. 24, 2012

(54) COATED TEST ELEMENTS

(75) Inventors: Rudolf Pachl, Ellerstadt (DE); Jürgen Hoferer, Karlsruhe (DE); Branislav Babic, Mannheim (DE); Martin Frank, Dirmstein (DE); Wilfried Schmid, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 873 days.

(21) Appl. No.: 10/581,409

(22) PCT Filed: Dec. 3, 2004

(86) PCT No.: PCT/EP2004/013782
§ 371 (c)(1),
(2), (4) Date: Sep. 20, 2006

(87) PCT Pub. No.: WO2005/054845
PCT Pub. Date: Jun. 16, 2005

(65) Prior Publication Data
US 2007/0110613 A1    May 17, 2007

(30) Foreign Application Priority Data
Dec. 4, 2003 (DE) .................. 103 56 752

(51) Int. Cl.
*G01N 33/48* (2006.01)
(52) U.S. Cl. ......... 436/63; 422/425; 422/430; 422/68.1; 422/412; 436/164; 436/169; 436/808
(58) Field of Classification Search .............. 422/425, 422/430, 68.1, 412; 436/63, 164, 169, 808
See application file for complete search history.

(56) References Cited

U.S. PATENT DOCUMENTS

| | | | |
|---|---|---|---|
| 4,301,115 A | 11/1981 | Rapkin et al. | |
| 4,312,834 A | 1/1982 | Vogel et al. | |
| 4,477,575 A | 10/1984 | Vogel et al. | |
| 5,279,791 A | 1/1994 | Aldrich et al. | |
| 6,228,927 B1 | 5/2001 | Lucarelli et al. | |
| 6,284,550 B1 | 9/2001 | Carroll et al. | |
| 6,441,898 B1 | 8/2002 | Markart | |
| 6,555,813 B1 | 4/2003 | Beecher et al. | |
| 6,605,471 B1 | 8/2003 | Lundsgaard et al. | |
| 6,660,363 B1 | 12/2003 | Barthlott | |
| 6,852,389 B2 | 2/2005 | Nun et al. | |
| 6,858,284 B2 | 2/2005 | Nun et al. | |
| 7,008,799 B1 | 3/2006 | Zimmer et al. | |
| 2002/0048679 A1 | 4/2002 | Lohmer et al. | |
| 2002/0084553 A1 | 7/2002 | Nun et al. | |
| 2002/0175802 A1 | 11/2002 | Horlebein | |

(Continued)

FOREIGN PATENT DOCUMENTS

CA    2095982    11/1993

(Continued)

OTHER PUBLICATIONS

Canadian Office Action mailed Feb. 26, 2009 received in corresponding CA patent application.

*Primary Examiner* — Lyle Alexander
(74) *Attorney, Agent, or Firm* — Bose McKinney & Evans LLP

(57) ABSTRACT

The invention concerns coated test elements and in particular test elements comprising a capillary gap which have a hydrophobic structured coating at least in the area surrounding the capillary gap.

18 Claims, 3 Drawing Sheets

U.S. PATENT DOCUMENTS

Figure 1:
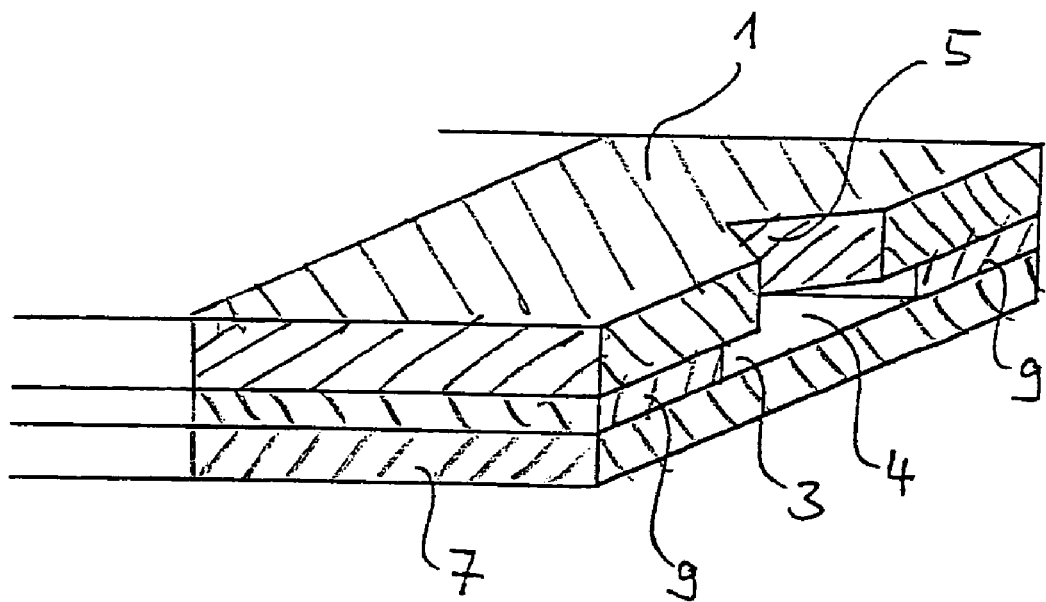

| | | |
|---|---|---|
| 2003/0013795 A1 | 1/2003 | Nun et al. |
| 2004/0168728 A1 | 9/2004 | Schober et al. |

FOREIGN PATENT DOCUMENTS

| | | |
|---|---|---|
| CA | 2260470 (A1) | 7/1999 |
| CA | 2302118 (A1) | 9/2000 |
| CA | 2302720 (A1) | 9/2000 |
| CA | 2368204 (A1) | 10/2000 |
| DE | 199 13 601 C1 | 8/2000 |
| DE | 199 17 367 A1 | 10/2000 |
| DE | 199 42 928 A1 | 4/2001 |
| DE | 199 42 928 C2 | 4/2001 |
| DE | 101 34 362 A1 | 1/2003 |
| DE | 101 38 036 A1 | 2/2003 |
| DE | 101 42 802 A1 | 3/2003 |
| EP | 0 010 456 A1 | 4/1980 |
| EP | 0 621 478 B1 | 10/1994 |
| EP | 0 878 537 A1 | 11/1998 |
| EP | 0 903 389 A1 | 3/1999 |
| EP | 1 152 242 B1 | 11/2001 |
| GB | 1335957 (A) | 10/1973 |
| JP | 2000-103882 | 5/2000 |
| JP | 2000-146892 | 5/2000 |
| WO | WO 99/36481 A1 | 7/1999 |
| WO | WO 00/39239 A1 | 7/2000 |
| WO | WO 00/58415 | 10/2000 |
| WO | WO 00/71834 | 11/2000 |

EXHIBIT A
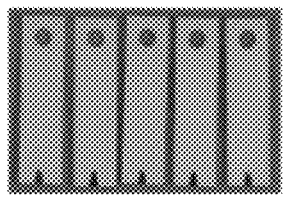
Lotus surface having elevations and depressions, the height of the elevations ranging from about 50 nm to 100 μm.
FIG. 3a
untreated surface
FIG. 3b
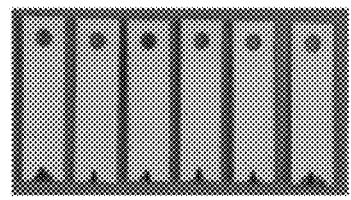
teflon surface
FIG. 3c

COATED TEST ELEMENTS

The invention concerns coated test elements in particular test elements comprising a capillary gap which have a hydrophobic structured coating at least in the area surrounding the capillary gap.

Test elements for diagnostic devices e.g. blood sugar measuring systems are often used by the patients themselves. The use generally involves applying a sample of body fluid e.g. blood to the test element, inserting the test element in a measuring device and determining an analyte from the body fluid in the measuring device. Previously it has been up to the user alone to decide about what happens to the excess sample material e.g. blood. When disposing of the test element, this sample material can be a serious contamination risk and a problem of hygiene depending on the disposal site. This problem was particularly relevant for test strips with a capillary gap in which blood often adhered to the outer side of the capillary.

The current trend in blood sugar measuring systems is to increasingly integrate the handling steps and system components. In this connection the test elements are often pulled into or through the measuring device. On its way through the device any sample material adhering to the outside of the test element carries the risk of contaminating the measuring instrument. There is a particular risk of contaminating the measuring instrument when the test strips are returned to the magazine. In doing so the test strips are transported within the measuring device after a sample has been applied to a test strip. Consequently there is a risk of contamination during the test element transport after a sample has been applied and also during storage of used test elements within the magazine. There is a risk that dried blood may fall off the test element and contaminate the magazine housing or contaminate test elements that are still to be used.

Another problem is that dried sample material on the outside of test elements can drop off in crumbs and contaminate instrument components, the optical system and the environment.

WO 97/46887 describes the return of cuvettes and test elements to a magazine. Surplus residual sample e.g. blood residues are collected by a protruding end of the test element to prevent contamination of the measuring device during restorage. However, this measure involves a complicated construction and does not reliably avoid contamination during restorage.

There is therefore a need for test elements and test procedures which prevent contamination by sample material especially during restorage to the largest possible extent. However, attempts to hydrophobically coat test elements with surfactants and waxes, with Teflon foils and sprays and with silicon-containing hydrophobizing agents have proven to be largely unsuccessful.

When test elements are coated with hydrophobic structured surfaces that are also known under the name lotus surfaces, it was surprisingly found that contamination with sample material, in particular with blood, can be substantially excluded. Especially in the case of test elements which have a channel opening or a gap for receiving and for transporting sample material, it was shown that lotus surfaces had the effect that only the channel opening or the gap is wetted. Moreover the coating with lotus surfaces has the advantage that an exact dosing and thus a reduction of the sample volume is possible which is described in detail in the following.

The lotus surface coating is particularly suitable for test elements with a hydrophilic capillary structure since a contamination of the edge area of the test elements and thus of the measuring instrument is liable to occur with such test elements. In such systems the test elements at first protrude from the instrument during blood application. The blood is applied by the user onto the end of the test element protruding from the instrument at which the capillary opening is located. When the test element has been coated with a lotus surface at least in the area of the opening, excess blood is either sucked into the capillary or drips from the edge of the test element so that only the capillary gap of the test element is wetted whereas no blood adheres to the area of the test element surrounding the capillary gap.

Hence a subject matter of the invention is an analytical test element for determining an analyte in a liquid comprising
  an inert carrier,
  an application zone for sample material,
  a detection zone for determining the analyte, and
  a channel or gap for transporting liquid from the application zone to the detection zone,
    wherein the test element has a hydrophobic structured surface at least in an area around the application zone.

Hydrophobic structured surfaces or lotus effect surfaces are self-cleaning surfaces which have elevations where the average distance between elevations is preferably in a range of 50 nm to 200 µm, particularly preferably in a range of 50 nm to 10 µm and the average height of the elevations is preferably in the range of 50 nm to 100 µm, particularly preferably in the range of 50 nm to 10 µm. Furthermore lotus effect surfaces are preferably characterized by a surface energy of less than preferably 20 mN/m and by a contact angle of preferably $\geq 120°$ and up to 160° with respect to aqueous systems. At least the elevations consist of hydrophobic materials such as nanoparticles with hydrophobic properties. Preferred examples of surfaces with the lotus effect are described in EP-B-0 772 514, EP-B-0 933 388, EP-A-1 018 531, EP-A-1 040 874, EP-B-1 171 529, EP-A-1 249 280 and EP-A-1 249 467 to the disclosure of which reference is herewith explicitly made.

Structured hydrophobic surfaces with a lotus effect can, as described in the above-mentioned documents, be produced by many different methods e.g. by coating, imbuing, spraying, coextruding or by injection moulding. It is preferred to spray on a suspension of hydrophobic nanoparticles.

A method is particularly preferred which comprises an fixation of the hydrophobic structured coating on the surface of the test element. In this case preferably at first a substance that can be hardened is applied to the areas of the test element that are to be coated, subsequently hydrophobic particles which preferably have cleft structures are applied to the coated areas and afterwards the particles are immobilized by hardening as described in EP-A-1 249 280. Lacquers which contain mono- or/and polyunsaturated acrylates or/and methacrylates or/and polyurethanes or/and silicon acrylates or/and urethane acrylates are for example suitable as hardenable substances. The lacquers preferably have hydrophobic properties. Particles may themselves be hydrophobic e.g. polymers in powder form and in particular halogenated hydrocarbons such as polytetrafluoroethylene or hydrophobized particles e.g. hydrophobic aerosils. The particles may also be optionally hydrophobized after immobilization on the carrier. The particles are immobilized by hardening for example by means of thermal or chemical energy or/and by light energy. A hydrophobic layer applied by such a multistep process is particularly resistant towards wear and mechanical stress.

The provision of a test element which has a lotus effect surface in an area around the application zone and in particular around a channel opening or a gap in the area of the application zone simplifies the dosing of the sample liquid since the sample liquid is automatically guided towards the channel opening and is prevented from adhering to the areas of the test element surrounding the channel opening. This is of particular interest for diabetic patients who are often older or visually impaired persons.

Since the hydrophobic structured surface allows an accurate dosing it is also possible to reduce the sample volume so that a relatively painless collection of only very small amounts of blood is possible. Moreover it has turned out that a hydrophobic coating of the test elements is advantageous especially for restorage of the test elements in a magazine. During such a restorage the test element which is firstly pushed out of a magazine that is optionally integrated into the measuring device for sample application e.g. to apply blood, is subsequently retracted again into this magazine. When the test element is coated according to the invention it turns out that there is no danger of a contamination of the outside.

The analytical test element coated according to the invention has a channel opening or a gap in the area of the application zone, wherein the surface of the test element has a hydrophobic structuring at least around the channel opening. If necessary the surface of the test element or at least the parts which are formed by the carrier as well as by covers or intermediate layers that may be present can be completely covered with a hydrophobically structured coating. The channel is preferably a capillary channel or capillary gap i.e. a channel or gap which is able to transport liquid by capillary action to the detection zone of the test element, and said channel or gap can optionally have an air-bleed hole at the other end in addition to an opening in the application zone. The interior of the channel has, preferably at least partially, a hydrophilic or hydrophilically coated surface e.g. a metallic or oxidic surface.

The channel or gap can in principle have any cross-section. The channel or gap preferably has an essentially rectangular cross-section, the dimensions of which are predetermined by the physical limits of capillary activity. The height of the channel or gap is for example of the order of magnitude of 10 to 500 µm, preferably between 20 and 300 µm for aqueous sample liquids. Depending on the desired channel or gap volume, the width can then be several millimeters, preferably 1 to 10 mm, particularly preferably 1 to 3 mm and the length can be up to a few cm, preferably 0.5 to 5 cm, especially preferably 1 to 3 cm.

The edge of the test element which forms the sample application zone preferably has a recess in the area which forms the channel or gap in order to facilitate entry of sample liquid into the channel. The dimensions of the recess e.g. its width is preferably selected such that the diameter of the drop of sample liquid that is applied to the test element is slightly larger than the chosen dimension of the recess. Thus a width of the recess of about 1 mm has proven to be suitable for a drop volume of 3 µl. The area exposed by the recess preferably has a hydrophilic or hydrophilically coated surface like the channel or gap itself.

In addition the test element contains some or all of the reagents required to determine the analyte and optionally auxiliary substances. These reagents include for example enzymes, enzyme substrates, indicators, buffer salts, inert fillers and such like. The reagents are preferably present in the area of the detection zone. The detection zone can be composed of one or more areas and usually contains absorbent materials that are impregnated with the reagents. Examples of absorbent materials are fleeces, fabrics, knitted fabrics or porous plastic materials that can for example be present in the form of layers. Preferred materials are papers or porous plastic materials such as membranes. The detection zone particularly preferably contains open films such as those described for example in EP-B-0 016 387. The films can consist of one or more layers and be applied to a carrier of the test element.

The detection zone can additionally have components which allow an exclusion of interfering sample components from the detection reaction and thus act as filters for example for particulate sample components such as blood cells. Suitable examples of this are semipermeable membranes or glass fibre fleeces such as those known from EP-B-0 045 476.

The analyte can be determined in the detection zone by optical methods e.g. by visual or photometric determination, by electrochemical methods or other suitable detection methods.

The test element can additionally contain covers or/and intermediate layers which together with the carrier and optionally the detection zone form the border of the sample transport channel or gap. The properties such as the material and coating of the covers and intermediate layers can be the same as or similar to that of the inert carrier. In this connection a flexible inert foil which extends over the entire length of the cover is particularly preferred on the side of the cover facing the channel or gap, said foil covering the entire width of the channel or gap and being at least partially enclosed between the opposing faces of the cover and detection element such that capillary liquid transport is not disrupted at the site of contact between the detection zone and cover.

Analytical test elements are particularly preferred with a capillary channel as described for example in WO 99/29429 to the disclosure of which reference is herewith explicitly made. These test elements are characterized by the fact that a channel or gap capable of capillary liquid transport is formed at least partially by the carrier and detection zone and extends in the direction of the capillary transport from the sample application zone at least to the edge of the detection zone, said edge being adjacent to the air-bleed opening in the test element and that a recess is located in an area forming the channel or gap which is capable of capillary liquid transport on the edge of the test element that forms the sample application opening such that one side of the edge of the test element that forms the sample application opening is at least partially discontinuous and the area opposite to the recess is exposed.

The coated test element according to the invention is preferably designed to be held within a magazine which can contain one or more test elements.

The test element is preferably designed to be returned to a magazine store i.e. to be held in a magazine which can contain both used and unused test elements where an unused test element is removed from the magazine before use and is returned again into the magazine after use. The removal or/and return can be carried out manually or automatically.

The individual test element can be a disposable test element or a test element that can be used several times. The magazine can be arranged within a measuring device which is for example designed for an optical or electrochemical detection.

The test element can be used to detect any analytes in liquid sample materials, in particular body fluids such as blood, saliva or urine. The determination of glucose in blood is particularly preferred. Other preferred examples for the use of the test elements are coagulation measurements or the measurement of HBA1C.

Another subject matter of the present invention is a measuring device for determining an analyte in a liquid which contains a coated test element according to the invention. The measuring device can integrally contain one or more magazines for holding one or more test elements. A measuring device with test elements reloaded into a magazine is preferred in which case used and unused test elements can be both present in a magazine.

Yet a further subject matter of the present invention is a method for determining an analyte in a liquid comprising
applying a sample liquid to a coated test element according to the invention and
qualitatively and/or quantitatively determining the analyte present in the sample liquid.

A volume of the sample liquid such as a volume of 1 to 10 µl is preferably applied to the test element. The application occurs in the area of the application zone of the test element where the surface is coated in a hydrophobically structured manner according to the invention at least in the area surrounding the application zone in order to prevent contamination by excess or/and inaccurately applied sample material.

The analyte is preferably determined in an integrated measuring device in which the test element is transported from a first position in the device e.g. in a first magazine to a second position e.g. a position for sample application, then to a third position e.g. a position for determining the analyte and then is removed from the device or transported to a fourth position e.g. in the first or another magazine. The device can contain one or more magazines which are each designed to hold one or more test elements. A device is particularly preferred with one magazine in which both used and unused test elements are present.

Preferred embodiments of the present invention are elucidated by the attached figures and examples:

FIG. 1 shows a detailed enlargement of a perspective view of a sample application zone in a particularly preferred embodiment of the test element according to the invention. The test element comprises a carrier (1) with a recess (5) which facilitates penetration of a sample liquid from the sample application zone (4) into a capillary-active channel (3) which in the present case is formed by the carrier (1), an intermediate layer (9) and a cover (7). The channel (3) leads to the detection zone of the test element (not shown). In addition to the shape shown, the recess can have any other shape which serves the purpose according to the invention.

The coating according to the invention can be present on the hatched surface areas of the carrier (1), of the cover (7), of the intermediate layer (9) and on the underside of the cover (7) which is not shown.

Figure 2:
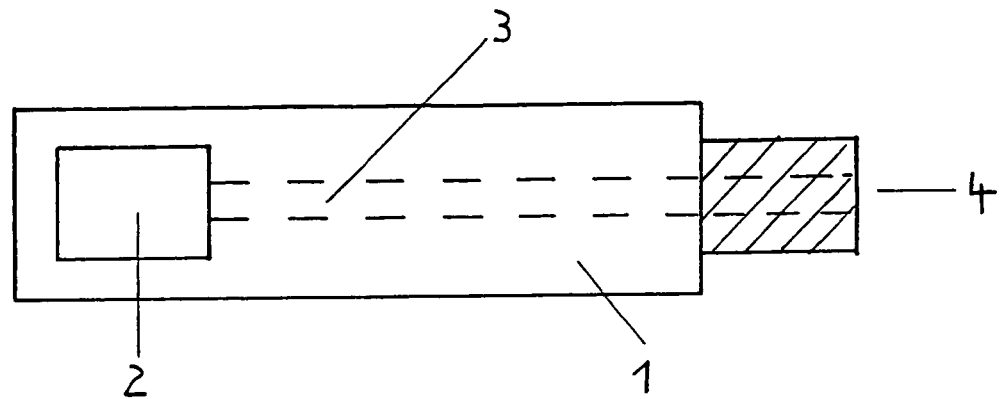
Figure 2:
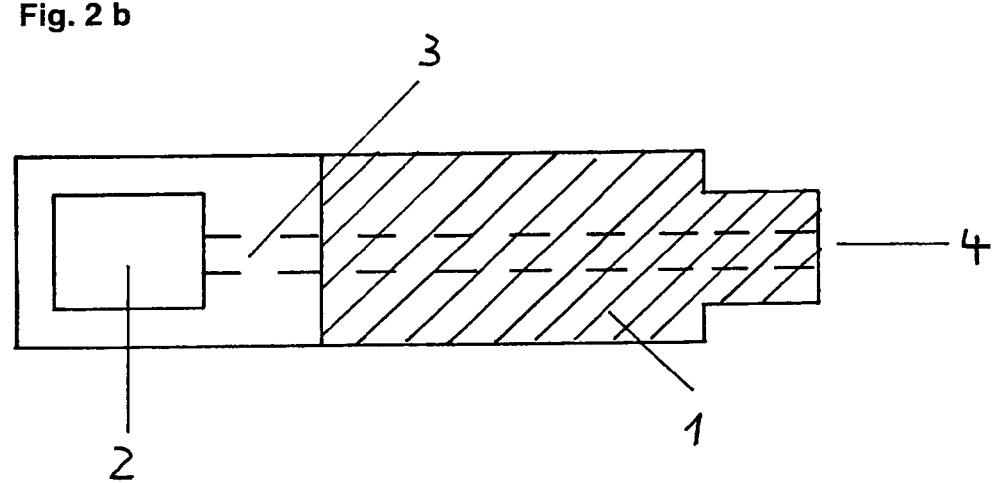

FIGS. 2a and b show examples of possible application areas for the coating according to the invention on a test element. The test element comprises a carrier (1), a detection zone (2) and a sample application zone (4) which is connected via a channel (3) to the detection zone (2). The coating according to the invention (indicated by the hatching) can— as shown in FIG. 2a—only be present on a limited part of the carrier in the area of the sample application zone (4) or—as shown in FIG. 2b—extend over most part of the test element.

FIG. 3 shows a comparison of blood uptake properties of test elements with a lotus effect surface (FIG. 3a), an untreated surface (FIG. 3b) and a Teflon-coated surface (FIG. 3c). The test elements have a sample application zone with a recess (below) which is connected via a capillary channel to a detection zone.

EXAMPLE

A test element produced according to WO 99/29429 was coated on the outside with a spray (lotus effect spray, Creavis) by means of which the surface of the carrier foil is coated with hydrophobic nanoparticles to form a hydrophobic structure with elevations. After a strip treated in this manner has been immersed in a 10 µl drop of blood, no blood is seen on the outside of the test element (FIG. 3a). In contrast strong contamination by blood was found in the area of the application zone in the case of a standard test element with a waxed outside (FIG. 3b) and a test element treated with a Teflon spray (FIG. 3c).

The invention claimed is:

1. An analytical test element for determining an analyte in a liquid, the test element comprising:
   an inert carrier supporting an application zone for sample material;
   a detection zone for determining the analyte;
   a channel formed to transport liquid from the application zone to the detection zone; and
   a hydrophobic structured surface formed in an area around the application zone, the hydrophobic structured surface comprising elevations and depressions, the height of the elevations ranging from about 50 nm to 100 µm;
   whereby, upon dosing of the test element, sample liquid is automatically guided towards the channel and is prevented from adhering to the hydrophobic structured surface formed in the area around the application zone.

2. The test element of claim 1, wherein the channel has an opening in the area of the application zone and the hydrophobic structured surface is positioned at least around the channel opening.

3. The test element of claim 1 wherein the channel is a capillary channel.

4. The test element of claim 1 wherein an interior of the channel has at least partially a hydrophilic surface.

5. The test element of claim 1 wherein the distance between elevations on the hydrophobic structured surface is about 50 nm to 200 µm.

6. The test element of claim 1 wherein the hydrophobic structured surface has a surface energy of $\leqq 20$ mN/m.

7. The test element of claim 1 wherein the hydrophobic structured surface has a contact angle with aqueous systems of $\geqq 120°$.

8. The test element of claim 1 wherein the hydrophobic structured surface is immobilized on the test element.

9. The test element of claim 1 wherein the test element is designed to be held within a magazine.

10. The test element of claim 9 wherein the magazine is designed to hold both used and unused test elements.

11. The test element of claim 9 wherein the magazine is located within a measuring device.

12. The test element of claim 11 wherein the measuring device is an optical or electrochemical measuring device.

13. The test element of claim 1 wherein the test element is designed to be contained in a measuring device.

14. The test element of claim 13 wherein the measuring device is an optical or electrochemical measuring device.

15. The test element of claim 1 wherein the test element is formed for determining glucose in blood.

16. A method for the determination of an analyte in a liquid, the method comprising:
    applying a sample liquid to a test element having an inert carrier supporting an application zone for sample material, a detection zone for determining the analyte, and a channel formed to transport liquid from the application zone to the detection zone, wherein the test element has a hydrophobic structured surface at least in an area around the application zone, the hydrophobic structured surface comprising elevations and depressions, the height of the elevations ranging from about 50 nm to 100 µm;

using the hydrophobic structured surface to guide the sample towards the channel while preventing the sample from adhering to the hydrophobic structured surface formed in the area around the channel; and qualitatively determining the analyte present in the sample liquid.

17. The method of claim 16 further comprising quantitatively determining the analyte present in the sample liquid.

18. A method for the determination of an analyte in a liquid, the method comprising:

applying a sample liquid to a test element having an inert carrier, an application zone for sample material, a detection zone for determining the analyte, and a channel formed to transport liquid from the application zone to the detection zone, wherein the test element has a hydrophobic structured surface at least in an area around the application zone, the hydrophobic structured surface comprising elevations and depressions, the height of the elevations ranging from about 50 nm to 100 μm;

using the hydrophobic structured surface to guide the sample towards the channel while preventing the sample from adhering to the hydrophobic structured surface formed in the area around the channel; and quantitatively determining the analyte present in the sample liquid.

* * * * *